United States Patent
Fukai

(10) Patent No.: US 6,332,370 B1
(45) Date of Patent: Dec. 25, 2001

(54) EVALUATION DEVICE FOR EVALUATING MIST GENERATION IN A VEHICLE LIGHTING DEVICE

(75) Inventor: Shingo Fukai, Shizuoka (JP)

(73) Assignee: Koito Manufacturing Co., Ltd., Tokyo (JP)

( * ) Notice: Subject to any disclaimer, the term of this patent is extended or adjusted under 35 U.S.C. 154(b) by 0 days.

(21) Appl. No.: 09/796,890

(22) Filed: Mar. 2, 2001

(51) Int. Cl.⁷ .................................................. G01N 25/00
(52) U.S. Cl. ............................................................ 73/865.6
(58) Field of Search ............................ 73/865.6; 356/121, 356/122

(56) References Cited

U.S. PATENT DOCUMENTS

| | | | |
|---|---|---|---|
| 1,961,347 | * 6/1934 | Godley | 356/122 |
| 2,887,779 | * 5/1959 | Hearn | 356/121 |
| 4,854,726 | * 8/1989 | Lesley et al. | 73/865.6 |
| 5,974,902 | * 11/1999 | Schofield | 73/865.6 |

FOREIGN PATENT DOCUMENTS

0204234 * 8/1988 (JP) ...................................... 73/865.6

* cited by examiner

*Primary Examiner*—Robert Raevis
(74) *Attorney, Agent, or Firm*—Sughrue Mion, PLLC

(57) ABSTRACT

An evaluation device for evaluating mist generation in a light chamber of a vehicle lighting device capable of obtaining a highly accurate result by a bench test. The evaluation device includes a partition wall that partitions a space outside of the lighting device into a front space and a rear space. Further, there is provided a rear space environment setting mechanism for setting the rear space at an environment different from that of the front space. Thus, even if the lighting device is not incorporated into a true vehicle, it is possible to make evaluations of mist generation while the environment in the space outside of the lighting device is maintained so as to be similar to that in a true vehicle.

6 Claims, 3 Drawing Sheets

EVALUATION DEVICE FOR EVALUATING MIST GENERATION IN A VEHICLE LIGHTING DEVICE

BACKGROUND OF THE INVENTION

1. Technical Field of the Invention

The present invention relates to an evaluation device for evaluating mist generation in a light chamber of a vehicle lighting device.

2. Related Art

In general, a vehicle lighting device includes a light chamber composed of a front lens and a lamp body. In many cases, at a rear portion of the lamp body, there is provided a vent hole for communicating the light chamber with an outer space of the lighting device. Due to the above structure, even when the lighting device is repeatedly turned on and off, the pressure in the lighting chamber is prevented from changing. Therefore, mist (as caused by moisture) is seldom created in the light chamber.

In the vehicle lighting device composed as described above, unless consideration is sufficiently given to the structure and arrangement of a vent hole, moisture gets into the light chamber from the outer space of the lighting device via the vent hole. When moisture gets into the light chamber, dew condensation is caused on the inner face of the lens, which results in the generation of mist.

Heretofore, it has been impossible to accurately evaluate the above generation of mist by using a bench test. Therefore, the evaluation of mist generation is made in such a manner that the lighting device is incorporated into a true vehicle and the generation of mist is evaluated while the vehicle is running.

SUMMARY OF THE INVENTION

1. Problems to be Solved by the Invention

However, according to the above-described mist evaluation method, it is necessary to attach the lighting device to a true car each time evaluation of mist generation is made. Therefore, it is not easy to repeatedly make evaluations of mist generation. Accordingly, it is difficult to obtain an accurate evaluation of mist generation in a short period of time.

The present invention has been accomplished in view of the above circumstances. It is an object of the present invention to provide an evaluation device for evaluating mist generation in a vehicle lighting device, wherein the evaluation device is capable of obtaining an accurate evaluation of mist generation by a bench test.

2. Manner of Solving the Problems

According to the present invention, the above and other objects can be accomplished by adopting an evaluation device, for evaluating mist generation in a vehicle lighting device, in which a predetermined partition wall is arranged so that different environments can be set in the front and the rear of the partition wall.

The present invention provides an evaluation device for evaluating mist generation in a vehicle lighting device, wherein the mist is generated in a light chamber of a vehicle lighting device that is composed of a front lens and a lamp body, the lamp body having a vent hole for communicating the light chamber with an outer space of the lighting device, the evaluation device comprising:

a partition wall that partitions the space outside of the lighting device into a front space and a rear space, wherein the partition wall is positioned at an outer circumferential section of the lighting device; and a rear space environment setting mechanism that sets the rear space at an environment different from that of the front space.

The vehicle lighting device, which is an object to be evaluated by the evaluation device of the present invention is not limited to a specific lighting device. That is, the lighting device may be a head lamp, a marker lamp, a fog lamp, a signal lamp, or the like.

A position of the above-described partition wall in the above "circumferential section of the lighting device" is not limited to a specific position. The position may be in the outer circumferential portion of the front lens. Alternatively, the position may be in the outer circumferential portion in the lamp body. In yet another alternative, the position may be located extending to both the front lens and the lamp body. However, from the viewpoint of evaluating mist generation in an environment which is similar to the environment in the outer space of the lighting device, it is preferable that the position of the partition wall is set along a boundary line between a portion exposed to the outer space of the vehicle body and a portion not exposed to the outer space of the vehicle body when the vehicle lighting device is attached to the vehicle body. In this connection, in general, the position of the boundary line is set at a position close to a joint face of the front lens and the lamp body.

The environment in the rear space, which is set by the above "rear space environment setting mechanism", is not limited to a specific environment as long as it is different from the environment in the front space. For example, it is possible to use an estimated environment in the engine room, or an estimated environment in the trunk room.

3. Action and Effect of the Invention

As shown in the above-described structure, according to the evaluation device for evaluating mist generation in a vehicle lighting device of the present invention, the space outside of the lighting device is partitioned into a front space and a rear space by the partition wall, so that the rear space can be set at an environment different from the environment in the front space. Therefore, even if the lighting device is not incorporated into a true car, evaluation of mist generation can be made under a condition approximating an environment in which the lighting device is incorporated into a true car.

Therefore, according to the present invention, even by a bench test, an accurate evaluation of mist generation can be made. Since the present invention makes it possible to evaluate the generation of mist by a bench test, it is possible to repeatedly make evaluations of mist generation in a short period of time. Due to the foregoing, evaluations of mist generation can be made at a low cost.

When a watering mechanism and an irradiating mechanism are arranged in the front space of the evaluation device so as to water the front lens and irradiate a beam of light for heating the front lens, it is possible to provide an environment which is similar to that in which the lighting device is mounted on a true car, which car is driven in rain, is washed by water, or is exposed to sunlight. Due to the foregoing, the accuracy of evaluating mist generation can be further enhanced.

In the above structure, the rear space environment setting mechanism comprises: an air current generator that generates a predetermined air current in the periphery of the lamp body; and a temperature and humidity control device that controls temperature and humidity in the rear space. Due to this structure, the environment in the rear space can be made similar to the environment in an engine room. Therefore, mist generation a head lamp can be highly accurately evaluated.

In this case, when the air current generator comprises a blast duct and a suction duct, when both the ducts are appropriately arranged, the air current close to the lamp body can be made similar to the air current of a true vehicle into which the lighting device is incorporated. Due to the foregoing, the accuracy of evaluating mist generation can be further enhanced.

BRIEF DESCRIPTION OF THE DRAWINGS

The above and other objects and advantages of the present invention will become more apparent by describing in detail a preferred exemplary embodiment thereof with reference to the accompanying drawings, wherein like reference numerals designate like or corresponding parts throughout the several views, and wherein.

DESCRIPTION OF A PREFERRED EMBODIMENT

Figure 1:
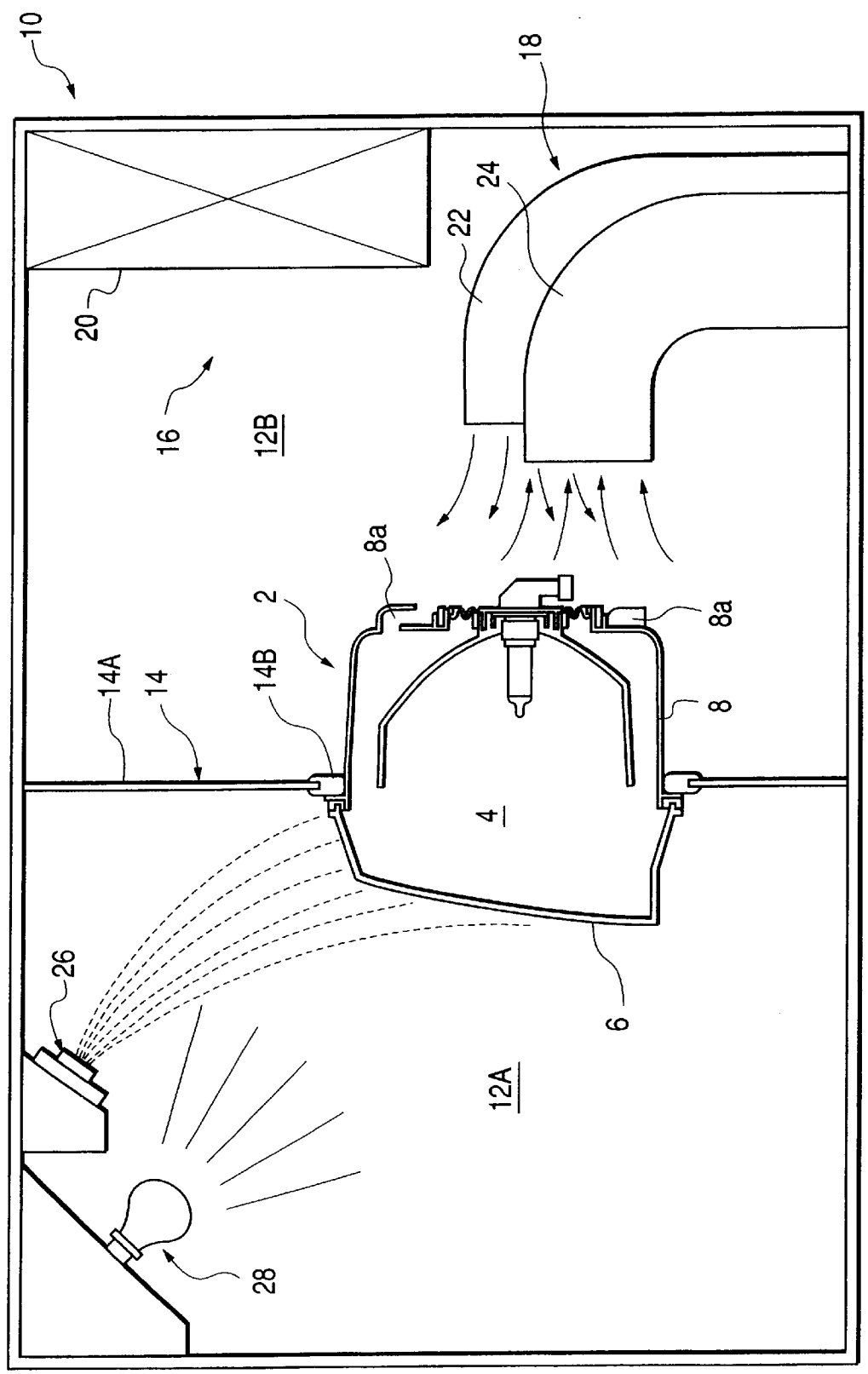
FIG. 1 is a cross-sectional side view showing an evaluation device, according to the present invention, for evaluating mist generation in a vehicle lighting device.

Referring to the drawings, an embodiment of the present invention will be explained below.

Figure 2:
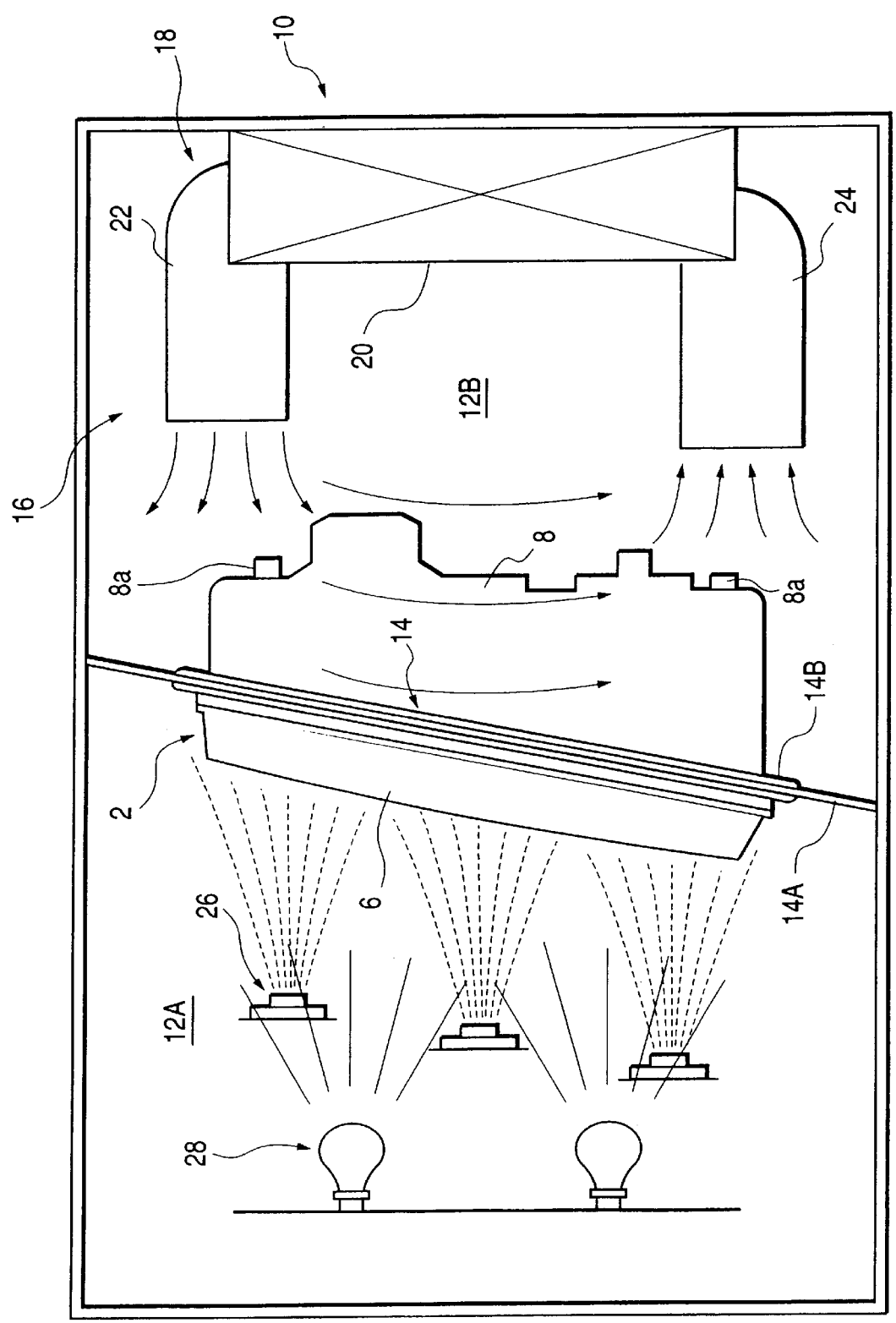
FIG. 2 is a top plan view showing the mist evaluation device.

FIGS. 1 and 2 are, respectively, a cross-sectional side view and a plan view showing an evaluation device 10 for evaluating mist generation in a vehicle lighting device, according to an embodiment of the present invention.

As shown in the drawing, this mist evaluation device 10 is a device for evaluating mist generated in the light chamber 4 of the vehicle lighting device 2. The vehicle lighting device 2, which is an object to be evaluated, is a head lamp. In this vehicle lighting device 2, the light chamber 4 is composed of a front lens 6 and a lamp body 8. In the lamp body 8, there is provided a plurality of vent holes 8a for communicating the inside of light chamber 4 with a space outside of the lighting device.

The mist evaluation device 10 includes: a partition wall 14 for partitioning the space outside of the lighting device into a front space 12A and a rear space 12B, wherein the partition is located at the periphery of a joint face between the front lens 6 and the lamp body 8; and a rear space environment setting mechanism 16 for setting the environment in the rear space 12B so that such environment is different from the environment in the front space 12A.

The partition wall 14 is composed of a partition wall body 14A, and a seal member 14B that is attached to the partition wall body 14A along the outer circumferential profile of the lamp body 8.

The rear space environment setting mechanism 16 includes: an air current generator 18 that generates a predetermined air current at a position close to the lamp body 8; and a temperature and humidity control device 20 that controls temperature and humidity in the rear space 12B.

The air current generator 18 includes a blast duct 22, and a suction duct 24. The blast duct 22 is arranged in such a manner that it opens forward at a position close to the outward end portion—in the vehicle width direction—of the vehicle lighting device 2. A current of air is blown out from the blast duct 22 toward the lamp body 8 by an air blast pump not shown in the drawing. On the other hand, the suction duct 24 is arranged in such a manner that it opens forward at a position close to the inner end portion—in the vehicle width direction—of the vehicle lighting device 2. A current of air is sucked from the rear space 12B by a suction pump not shown in the drawing. A current of air along the lamp body 8 is thusly generated by the blast duct 22 and the suction duct 24.

Figure 3:
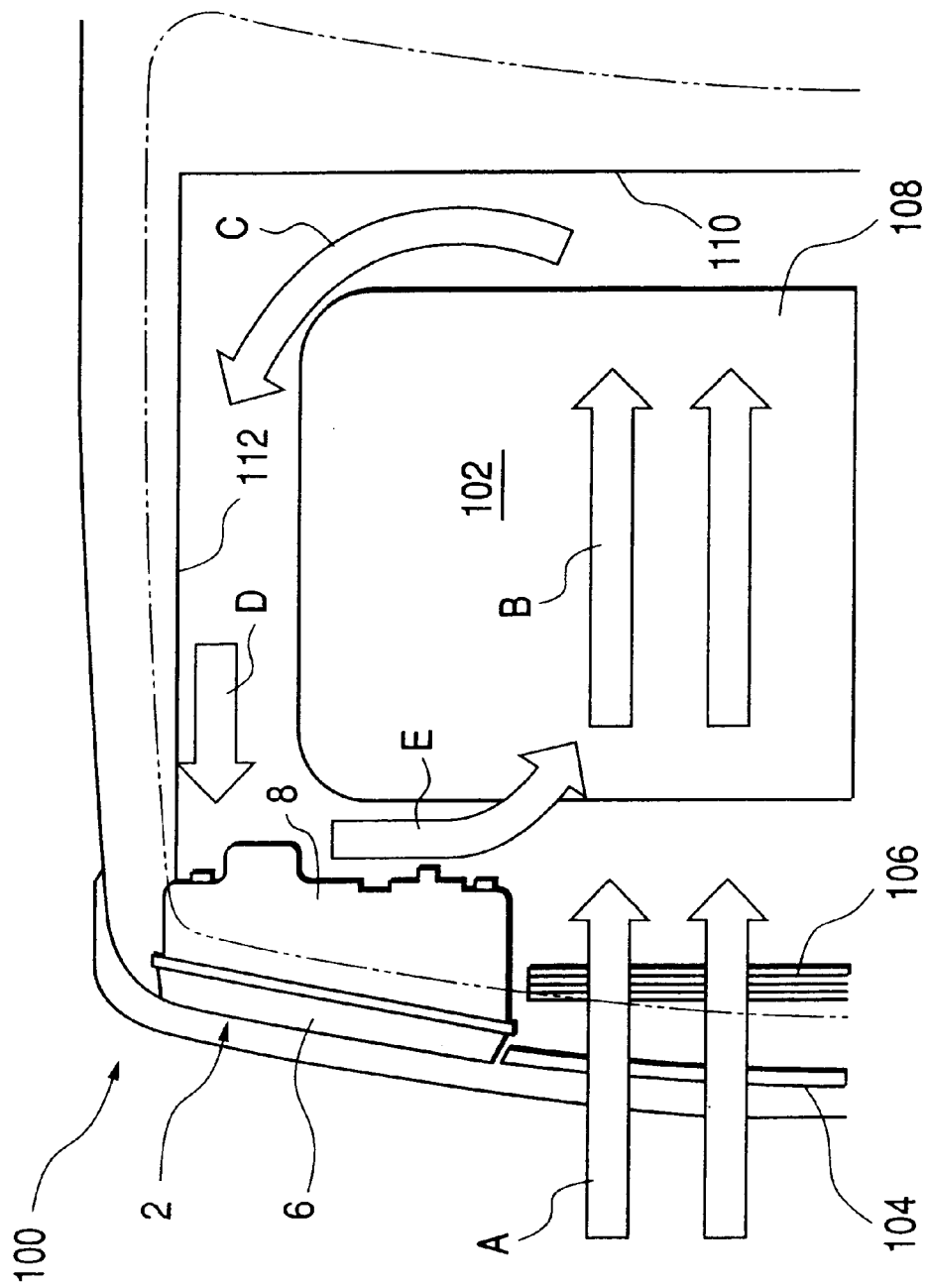
FIG. 3 is a top plan view showing a state of an air current in an engine room of a vehicle.

Referring to FIG. 3, the reason why the above air currents are generated will be explained below.

FIG. 3 is a top plan view showing air currents in the engine room 102 of the vehicle 100.

As shown in the drawing, wind—caused when the vehicle is running—flows into the engine room 102 via the front grill 104 and the radiator 106 as shown by arrow A. Even if the vehicle is stopped, when the engine 108 is running, outside air is forcibly sucked into the engine room 102 by the radiator fan as shown by arrow A. This current of air flowing into the engine room 102 flows backward along the engine 108 as shown by arrow B. After that, the current of air collides with the dash panel 110 as shown by arrow C and is curved to the right and left so that it is returned forward along the fender panel 112. As shown by arrow D, the current of air collides, from the rear side, with an outside end portion—in the vehicle width direction—of the lamp body 8 of the vehicle lighting device 2 for. Then, as shown by arrow E, the current of air flows inward—in the vehicle width direction—along the lamp body 8. After that, the current of air shown by arrow E joins to the current of air shown by arrow B.

In this embodiment of the present invention, the same current of air—as that flowing along the lamp body 8 generated in the engine room 102—is created by the blast duct 22 and the suction duct 24.

In FIGS. 1 and 2, the rear space 12B, of the mist evaluation device 10, includes a constant temperature and humidity tank. The constant temperature and humidity section includes a temperature and humidity control device 20. This temperature and humidity control device 20 controls temperature and humidity in the rear space 12B according to a program so that the same temperature and humidity as those in the engine room of a true vehicle—which true-vehicle temperature and humidity have previously been measured—can be obtained.

In the front space 12A, of the mist evaluation device 10, there are provided a watering mechanism 26 for watering the front lens 6, and an irradiating mechanism 28 for irradiating a beam of light to heat the front lens 6. The watering mechanism 26 sprays water, which has been supplied from a water supply not shown in the drawing, by a plurality of nozzles. A quantity of water to be sprayed can be appropriately adjusted. The irradiating mechanism 28 is composed of a plurality of incandescent lamps, which conduct beam irradiation when they are turned on. The irradiation time can be appropriately adjusted.

As described above in detail, the evaluation device 10 of this embodiment is composed in such a manner that the space outside of the lighting device is partitioned into the front space 12A and the rear space 12B by the partition wall 14, and the environment in the rear space 12B can be set at a different environment from that of the all front space 12A by the rear space environment setting mechanism 16. Therefore, unlike the conventional evaluation method, even if the lighting device is not incorporated into a true vehicle, it is possible to make an evaluation of mist generation in an environment approximating an environment in which the lighting device is incorporated into a true vehicle.

Consequently, according to the present invention, it is possible to obtain an accurate result of mist evaluation by a bench test. Since evaluation of mist generation can be made by a bench test, as described above, it is possible to frequently make evaluations of mist generation in a short period of time. Therefore, it is possible to make evaluations of mist generation at a low cost.

Further, in this embodiment, the watering mechanism 26 and the irradiating mechanism 28 are arranged in the front space 12A. Therefore, the front lens 6 can be watered by the watering mechanism 26, and can be irradiated with a beam of light by the irradiating mechanism 28. Accordingly, it is possible to obtain an environment similar to one in which the lighting device is incorporated into a true vehicle that is driven in rain, that is washed by water, or that is exposed to sunlight.

In this embodiment, the rear environment setting mechanism 16 includes: an air current generator 18 that generates a predetermined air current in the periphery of the lamp body 8; and a temperature and humidity control device 20 that controls temperature and humidity in the rear space 12B. Therefore, it is possible to make the environment in the rear space 12B similar to the environment in an engine room. Due to the foregoing, it is possible to enhance the accuracy of evaluating mist generation for the head lamp, or the vehicle lighting device 2.

Further, the air current generator 18 generates an air current that moves inward—in the vehicle width direction—long the lamp body 8 by use of a blast duct 22 and a suction duct 24. Accordingly, the air current generated in the periphery of the lamp body 8 can be made very similar to the air current actually generated in a true vehicle. Due to the foregoing, the accuracy of evaluating mist generation can be further enhanced.

In the above embodiment, explanation is made with respect to a case in which the lighting device 2 is an object that is subjected to evaluation of mist generation. However, when the same structure as that of the above embodiment is applied to an auxiliary head lamp, such a fog lamp, and also when the same structure as that of the above embodiment is applied to a marker lamp, such as a front turn signal lamp, or a rear combination lamp, the same action and effect as that of the above embodiment can be provided.

What is claimed is:

1. An evaluation device for evaluating mist generation in a vehicle lighting device, the mist being generated in a light chamber of the vehicle lighting device that is composed of a front lens and a lamp body, the lamp body having a vent hole for communicating the light chamber with a space outside of the lighting device, the evaluation device comprising:

a partition wall that partitions the space outside of the lighting device into a front space and a rear space, wherein the partition wall is positioned at an outer circumferential section of the lighting device;

a rear space environment setting mechanism that sets the rear space at an environment different from that of the front space; and a watering mechanism that is adapted to water the front lens, said watering mechanism being arranged in the front space.

2. An evaluation device for evaluating mist generation in a vehicle lighting device according to claim 1, wherein said evaluation device is further comprising an irradiating mechanism that is adapted to irradiate a beam of light to heat the front lens, said irradiating mechanism being arranged in the front space.

3. An evaluation device for evaluating mist generation in a vehicle lighting device according to claim 1 or 2, wherein the rear space environment setting mechanism comprises:

an air current generator that generates a predetermined air current in the periphery of the lamp body; and a temperature and humidity control device that controls temperature and humidity in the rear space.

4. An evaluation device for evaluating mist generation in a vehicle lighting device according to claim 3, wherein the air current generator includes a blast duct and a suction duct.

5. An evaluation device for evaluating mist generation in a vehicle lighting device according to claim 1, wherein the rear space environment setting mechanism comprises:

an air current generator that generates a predetermined air current in the periphery of the lamp body; and a temperature and humidity control device that controls temperature and humidity in the rear space.

6. An evaluation device for evaluating mist generation in a vehicle lighting device according to claim 5, wherein the air current generator includes a blast duct and a suction duct.

* * * * *